US010448895B2

United States Patent
Tathireddy et al.

(10) Patent No.: US 10,448,895 B2
(45) Date of Patent: Oct. 22, 2019

(54) SENSOR SYSTEMS

(71) Applicant: University of Utah Research Foundation, Salt Lake, UT (US)

(72) Inventors: Prashant Tathireddy, Salt Lake City, UT (US); Carlos Mastrangelo, Salt Lake City, UT (US); Florian Solzbacher, Salt Lake City, UT (US); Nassir Marrouche, Park City, UT (US); Jules Magda, Salt Lake City, UT (US)

(73) Assignee: UNIVERSITY OF UTAH RESEARCH FOUNDATION, Salt Lake City, UT (US)

( * ) Notice: Subject to any disclaimer, the term of this patent is extended or adjusted under 35 U.S.C. 154(b) by 718 days.

(21) Appl. No.: 14/774,070

(22) PCT Filed: Mar. 11, 2014

(86) PCT No.: PCT/US2014/023352
§ 371 (c)(1),
(2) Date: Sep. 9, 2015

(87) PCT Pub. No.: WO2014/164731
PCT Pub. Date: Oct. 9, 2014

(65) Prior Publication Data
US 2016/0015323 A1    Jan. 21, 2016

Related U.S. Application Data

(60) Provisional application No. 61/851,603, filed on Mar. 11, 2013, provisional application No. 61/927,683, filed on Jan. 15, 2014.

(51) Int. Cl.
*A61B 5/145* (2006.01)
*A61B 5/00* (2006.01)
(Continued)

(52) U.S. Cl.
CPC .............. *A61B 5/6852* (2013.01); *A61B 5/05* (2013.01); *A61B 5/14503* (2013.01);
(Continued)

(58) Field of Classification Search
None
See application file for complete search history.

(56) References Cited

U.S. PATENT DOCUMENTS

| 3,674,012 A | 7/1972 | Sage |
|---|---|---|
| 3,841,307 A | 10/1974 | Friedell |

(Continued)

FOREIGN PATENT DOCUMENTS

| BR | 11/150220576 | 3/2014 |
|---|---|---|
| CN | 201480013762.3 | 3/2014 |

(Continued)

OTHER PUBLICATIONS

International Search Report mailed by the International Searching Authority dated Aug. 5, 2014 for international application PCT/US2014/023352, filed on Mar. 11, 2014, and published as WO 2014/164731 on Oct. 9, 2014 (Applicant—University of Utah Research Foundation // Inventor—Tathireddy, et al.) (2 pages).

(Continued)

*Primary Examiner* — Eric F Winakur
*Assistant Examiner* — Marjan Fardanesh
(74) *Attorney, Agent, or Firm* — Workman Nydegger

(57) ABSTRACT

A sensor sheath for a catheter. The sensor sheath includes a substrate having at least one sensor associated therewith; and an electronics unit in communication with at the at least one sensor, wherein the substrate is configured to attach to a catheter.

13 Claims, 14 Drawing Sheets

(51) Int. Cl.
*A61B 5/05* (2006.01)
*H01F 1/00* (2006.01)
*G01N 33/543* (2006.01)

(52) U.S. Cl.
CPC ...... *A61B 5/14532* (2013.01); *A61B 5/14539* (2013.01); *A61B 5/14542* (2013.01); *A61B 5/14546* (2013.01); *A61B 5/4842* (2013.01); *A61B 5/4848* (2013.01); *A61B 5/686* (2013.01); *G01N 33/54373* (2013.01); *H01F 1/0045* (2013.01); *A61B 2562/0223* (2013.01); *A61B 2562/0285* (2013.01); *A61B 2562/063* (2013.01); *A61B 2562/066* (2013.01)

(56) References Cited

U.S. PATENT DOCUMENTS

| | | |
|---|---|---|
| 4,949,722 A | 8/1990 | Bean et al. |
| 5,415,864 A | 5/1995 | Kopecek et al. |
| 5,427,144 A | 6/1995 | Teets et al. |
| 5,447,727 A | 9/1995 | Graham |
| 5,662,107 A | 9/1997 | Sakariassen |
| 6,146,327 A | 11/2000 | Wilk |
| 6,198,950 B1 | 3/2001 | Kraus |
| 6,268,161 B1 | 7/2001 | Han et al. |
| 6,333,109 B1 | 12/2001 | Harada et al. |
| 6,464,699 B1 | 10/2002 | Swanson |
| 6,475,750 B1 | 11/2002 | Han et al. |
| 6,514,689 B2 | 2/2003 | Han et al. |
| 6,615,071 B1 | 9/2003 | Casscells, III et al. |
| 6,709,390 B1 | 3/2004 | Marie Pop |
| 6,753,191 B2 | 6/2004 | Asher et al. |
| 6,835,553 B2 | 12/2004 | Han et al. |
| 6,848,384 B2 | 2/2005 | Higgins et al. |
| 6,980,853 B2 | 12/2005 | Miyoshi et al. |
| 7,150,975 B2 | 12/2006 | Tamada et al. |
| 7,179,487 B1 | 2/2007 | Kopecek et al. |
| 7,556,934 B2 | 7/2009 | Ragless |
| 7,625,951 B2 | 12/2009 | Daunert et al. |
| 7,857,761 B2 | 12/2010 | Lee et al. |
| 7,892,188 B2 | 2/2011 | Walker et al. |
| 7,985,213 B2 | 7/2011 | Parker |
| 7,988,685 B2 | 8/2011 | Ziaie et al. |
| 8,003,373 B2 | 8/2011 | Soykan et al. |
| 8,221,773 B2 | 7/2012 | Schneider et al. |
| 8,265,745 B2 | 9/2012 | Hauck et al. |
| 8,277,384 B2 | 10/2012 | Fine |
| 8,283,384 B2 | 10/2012 | Stewart et al. |
| 8,317,737 B2 | 11/2012 | Hyde et al. |
| 8,324,184 B2 | 12/2012 | Prestwich et al. |
| 8,328,720 B2 | 12/2012 | Mir et al. |
| 8,382,987 B2 | 2/2013 | Luchini et al. |
| 2005/0033136 A1 | 2/2005 | Govari et al. |
| 2005/0169882 A1 | 8/2005 | Lowe et al. |
| 2006/0239986 A1 | 10/2006 | Perez-Luna et al. |
| 2007/0248993 A1 | 10/2007 | Seul et al. |
| 2008/0044472 A1 | 2/2008 | Garcia et al. |
| 2008/0188928 A1 | 8/2008 | Salahieh et al. |
| 2008/0206894 A1 | 8/2008 | Lyon et al. |
| 2008/0275171 A1 | 11/2008 | Song et al. |
| 2008/0311670 A1 | 12/2008 | Zhu |
| 2009/0105799 A1 | 4/2009 | Hekmat et al. |
| 2009/0170209 A1 | 7/2009 | Machauf et al. |
| 2009/0215923 A1 | 8/2009 | Carnahan et al. |
| 2009/0240121 A1 | 9/2009 | Bickoff |
| 2010/0285094 A1 | 11/2010 | Gupta |
| 2010/0286497 A1 | 11/2010 | Fine et al. |
| 2011/0033947 A1 | 2/2011 | Nakahama |
| 2011/0034908 A1 | 2/2011 | Hyde et al. |
| 2011/0044932 A1 | 2/2011 | Carnahan et al. |
| 2011/0053173 A1 | 3/2011 | Hood et al. |
| 2011/0053283 A1 | 3/2011 | Hood et al. |
| 2011/0054938 A1 | 3/2011 | Hood et al. |
| 2011/0082412 A1 | 4/2011 | Hyde et al. |
| 2011/0095756 A1 | 4/2011 | Van Bruggen et al. |
| 2011/0275985 A1 | 11/2011 | Lowery, Jr. et al. |
| 2011/0280914 A1 | 11/2011 | Prestwich et al. |
| 2012/0029430 A1 | 2/2012 | Banister et al. |
| 2012/0035434 A1 | 2/2012 | Ferren et al. |
| 2012/0035437 A1 | 2/2012 | Ferren et al. |
| 2012/0035438 A1 | 2/2012 | Ferren et al. |
| 2012/0035439 A1 | 2/2012 | Ferren et al. |
| 2012/0035440 A1 | 2/2012 | Ferren et al. |
| 2012/0035540 A1 | 2/2012 | Ferren et al. |
| 2012/0041291 A1 | 2/2012 | Ferren et al. |
| 2012/0078068 A1 | 3/2012 | Ulmer |
| 2012/0170050 A1 | 7/2012 | Savran et al. |
| 2012/0172703 A1 | 7/2012 | Esguerra et al. |
| 2012/0223705 A1 | 9/2012 | Lowery et al. |
| 2012/0234465 A1 | 9/2012 | Wen et al. |
| 2013/0129797 A1 | 5/2013 | Gupta et al. |
| 2013/0143821 A1 | 6/2013 | Magda et al. |
| 2013/0144137 A1 | 6/2013 | Zalevsky et al. |
| 2013/0172985 A1 | 7/2013 | Prestwich et al. |
| 2013/0245402 A1* | 9/2013 | Ziaie .................. G01N 27/72 600/309 |
| 2013/0267455 A1 | 10/2013 | Hauser et al. |

FOREIGN PATENT DOCUMENTS

| | | |
|---|---|---|
| EP | 1225940 A2 | 7/2002 |
| EP | 14780278.9 | 3/2014 |
| IN | 2627/MUMNP/15 | 3/2014 |
| KR | 1020157024727 | 3/2014 |
| RU | 2015138942 | 3/2014 |
| WO | WO-01/28606 A2 | 4/2001 |
| WO | WO-2008/135916 A1 | 11/2008 |
| WO | WO-2012/170401 A2 | 12/2012 |
| WO | PCT/US2014/023352 | 3/2014 |
| WO | WO-2014/164731 A1 | 10/2014 |

OTHER PUBLICATIONS

Supplementary European Search Report dated Oct. 18, 2016, for application EP 14780278.9, filed on Mar. 11, 2014, and published as EP 2967414 on Jan. 20, 2016 (Applicant—Univ. of Utah Research Foundation // Inventor—Prashant Tathireddy, et al.) (6 pages).
Adrus, M. Ulbricht, "Molecularly imprinted stimuli-responsive hydrogels for protein recognition", Polymer 53, 4359-4366 (2012).
Arakawa, et al., "A Drug-Injection System with Chem-Mechanical Enery Conversion for Active Feedback Control of Glucose Concentration in a Blood," Transducers'11, Beijing, China, Jun. 5-9, 2011 (4 pages).
Beebe, et al., "Functional hydrogel structures for autonomous flow control inside microfluidic channels," Nature, vol. 404 (2000) (3 pages).
Bini et al. "Analytical Performance of Aptamer-Based Sensing for Thrombin Detection", Anal Chem 79, 3016-3019 (2007).
Brazier, J.J., Yan, M., "Micromonoliths and Microfabricated Molecularly Imprinted Polymers," Ch. 19 in Molecularly Imprinted Materials, Yan, M.., Ramstrom, O., editors, NYC, USA, Marcel Dekker, 2005 (28 pages).
Cajlakovic, "Continuous monitoring of pO2 and pCO2 by microdialysis indicates physiologic status of the critically ill patients," Sensors and Actuators B 139 (2009) 181-186.
Chan, et al., "Scanning Magnetic Tunnel Junction Sensor for the Detection of Magnetically Labeled DNA Microarray," 14th International Conference on Solid-state Sensors, Actuators and Microsystems, Jun. 2007 (4 pages).
Chen, et al., "A Glucose-Responsive Insulin Delivery Micro Device Embedded with Nanohydrogel Particles as "Smart Valves"," Transducers 11, Beijing, China, Jun. 5-9, 2011 (4 pages).
Cimen et al. "Molecularly imprinted hydrogels for fibrinogen recognition", Reactive and Functional Polymers DOI: 10.1016/j.reactfunctpolym.2009.04.009 (5 pages).
De Volder, et al., "Hygroscopic Biomimetic Transducers Made from CNT-Hydrogel Composites," Transducers'11, Beijing, China, Jun. 5-9, 2011 (4 pages).

(56) References Cited

OTHER PUBLICATIONS

Eppler et al., "A strategy for high-throughput screening of ligands suitable for molecular imprinting of proteins", Biosensors & Bioelectronics 35, 27-32 (2012).
Gehrke, "A strategy for high-throughput screening of ligands suitable for molecular imprinting of proteins," Responsive Gels: Volume Transitions II, pp. 81-144, 1993.
Han, et al., "Constant-Volume Hydrogel Osmometer: A New Device Concept for Miniature Biosensors," Biomacromolecules 2002, 3, 1271-1275.
Hendrickson, et al., "Bioresponsive hydrogels for sensing applications," Soft Matter, 2009, 5, 29-35.
Heo, et al., "Fluorescent Hydrogel Fibers for Long-Term in vivo Glucose Monitoring," Transducers 11, Beijing, China, Jun. 5-9, 2011 (4 pages).
Herber, "Development of a Hydrogel-Based Carbon Dioxide Sensor—a tool for diagnosing gastrointestinal ischemia," (2005) (174 pages).
Herber, et al., "A Miniaturized Carbon Dioxide Gas Sensor Based on Sensing of pH-Sensitive Hydrogel Swelling with a Pressure Sensor," Biomedical Microdevices 7:3, 197-204, 2005.
Herber, et al., "A swelling hydrogel-based PCO2 sensor," Sensors and Actuators B 91 (2003) 378-382.
Herber, et al., "Micro CO2 Gas Sensor Based on Sensing of Ph-Sensitive Hydrogel Swelling by means of a Pressure Sensors," 13th International Conference on Solid-state Sensors, Actuators and Microsystems, Seoul, Korea, Jun. 5-9, 2005 (4 pages).
Herber, et al., "Study of chemically induced pressure generation of hydrogels under isochoric conditions using a microfabricated device," J. Chem. Physics vol. 121, No. 6 (2004) (6 pages).
Hilt, et al., "A Microsensor Based on a Microcantilever Patterned with an Environmentally Sensitive Hydrogel," Mat. Res. Soc. Symp. Proc. vol. 729 2002 (6 pages).
Huang, et al., "A dielectric affinity microbiosensor," Applied Physics Letters 96, 033701 2010 (3 pages).
Huang, et al., "A MEMS Differential Affinity Sensor for Continuous Glucose Detection," Transducers'11, Beijing, China, Jun. 5-9, 2011 (4 pages).
Huang, et al., "A MEMS affinity glucose sensor using a biocompatible glucose-responsive polymer," Sensors and Actuators B 140 (2009) 603-609.
Ibrahim M, and Hugh D C Smyth. "Smart Magnetically Responsive Hydrogel Nanoparticles Prepared by a Novel Aerosol-Assisted Method for Biomedical and Drug Delivery Applications." Journal of Nanomaterials (2011): 1-13.
Ionescu, et al., "Detection of endogenous magnetic nanoparticles with a tunneling magneto resistance sensor," Phil. Trans. R. Soc. A 2010 368, 4371-4387.
Jackson, M.P. Esnouf, "Has the Time Arrived to Replace the Quick Prothrombin Time Test for Monitoring Oral Anticoagulant Therapy?", Clinical Chem 51, 483-485 (2005).
Koschwanez, et al., "In vitro, in vivo and post explanation testing of glucose-detecting biosensors: Current methods and recommendations," Biomaterials 28 (2007) 3687-3703.
Lei, et al., "A Hydrogel-Based Implantable Micromachined Transponder for Wireless Glucose Measurement," Diabetes Tech. and Therapeutics, vol. 8, No. 1 (2006) (11 pages).
Liao et al., "Molecularly imprinted aptamers of gold nanoparticles for the enzymatic inhibition and detection of thrombin", Langmuir 28, 8944-51 (2012).
Lin, et al., "Free swelling and confined smart hydrogels for applications in chemomechanical sensors for physiological monitoring," Sensors and Actuators B 136 (2009) 186-195.
Lin, et al., "Osmotic swelling pressure response of smart hydrogels suitable for chronically implantable glucose sensors," Sensors and Actuators (2009) (5 pages).
Liu, et al., "A CMOS Hall-Effect Sensor for the Characterization and Detection of Magnetic Nanoparticles for Biomedical Applications," IEEE Transactions of Magnetics, vol. 47, No. 10 Oct. 2011 (3 pages).

Mariserla, et al., "A Novel Glucoe Sensor Based on Deflection of a Thin Membrane," 2005 ASME Int'l Mech. Engineering Congress and Exposition (2 pages).
Millet, et al., "Characterization of Mass and Swelling of Hydrogel Microstructures using MEMS Resonant Mass Sensor Arrays," Small 2012, 8, No. 16, 2555-2562.
Miyata et al. "Responsive behavior of tumor-markeri-mprinted hydrogels using macromolecular cross-linkers", J. Mol. Recognit. 25, 336-343 (2012).
Niu et al., "Turn-on colorimetric sensor for ultrasensitive detection of thrombin using fibrinogen-gold nanoparticle conjugate", Analyst 138, 1475-82 (2013).
Oliver, et al., "Glucose sensors: a review of current and emerging technology," Diabetic Medicine, 26, 197-210 (2009).
Peppas, et al., "Hydrogels in Biology and Medicine: From Molecular Principles to Bionanotechnology," Adv. Mater. 2006, 18, 1345-1360.
Richter, et al., "Review on Hydrogel-based pH Sensors and Microsensors," Sensors 2008, 8, 561-581.
Siegel, et al., "Hard and soft micro- and nanofabrication: An integrated approach to hydrogel-based biosensing and drug delivery," Journal of Controlled Release 141 (2010) 303-313.
Solomon, et al. "The Diagnostic Accuracy of Bedside and Laboratory Coagulation", Coagulation and Transfusion Medicine, 109, 371-378 (1998).
Soon, et al., "A Novel Microneedle-Based Non_Enzymatic Glucose Sensor for Painless Diabetes Testing Application," Transducers'11, Beijing, China, Jun. 5-9, 2011 (4 pages).
Sridhar, et al., "A hydrogel-based passive wireless sensor using a flex-circuit inductive transducer," Sensors and Actuators A 155 (2009) 58-65.
Steege, et al., "Assessment of a new prototype hydrogel CO2 sensor; Comparison with air tonometry," J. Clinical Monitoring nd Computing (2007) vol. 21, pp. 83-90.
Suh, et al., "Synthesis of magnetic hydrogel microparticles for bioassays and tweezer manipulation in microwells," Microfluid Nanofluid (2012) (10 pages).
Trinh, et al., "Hydrogel-based piezoresistive pH sensors: Design, simulation and output characteristics," Sensors and Actuators B 117 (2006) 17-26.
van den Berg, et al., "Silicon for the perfect membrane," Nature, vol. 445, Feb. 15, 2007 (1 page).
Vékás, Ladislau. "Ferrofluids and Magnetorheological Fluids." Advances in Science and Technology 54 (2008): 127-136.
Wang, Yi. "New Biosensor Applications of Surface Plasmon and Hydrogel Optical Waveguide Spectroscopy." PhD Dissertation, (2010) (141 pages).
Yu, et al., "An Integrated Microfluidic System for Interstitial Fluid Transdermal Extraction," Transducers 11, Beijing, China, Jun. 5-9, 2011 (4 pages).
Yu, et al., "Transcutaneous Implantation Methods for Improving the Long-Term Performance of Glucose Sensors in Rats," IEEE Sensors Journal vol. 8, No. 1, Jan. 2008 (7 pages).
Keller, P. (2011) "NMR magnetometers, Magnetics Technology International", (pp. 68-71) available at http://www.gmw.com/magnetic_measurements/MetroLab/pdf/MagneticsTechnologyInternational-2011-MetrolabNMR.pdf.
Miyata, et al., (1999) "A reversibly antigen-responsive hydrogel", Nature, vol. 399(6738), (pp. 766-769).
Park, et al., (2013) "A Wireless Chemical Sensor Using Ferroparticles Embedded Hydrogel", Solid-State Sensors, Actuators and Microsystems, Transducers & Eurosensors XXVII: The 17th International Conference (4 pages).
Satarkar, et al., (2010) "Hydrogel Nanocomposites: A Review of Applications as Remote Controlled Biomaterials", Soft Matter, vol. 6, (pp. 2364-2371).
Siegel, et al., (1988) "pH-dependent equilibrium swelling properties of hydrophobic polyelectrolyte copolymer gels", Macromolecules, vol. 21, (pp. 3254-3259).
Song, et al., (2014) "A wireless chemical sensor featuring iron oxide nanoparticle-embedded hydrogels", Sensors and Actuators B 193 (pp. 925-930).

(56) References Cited

OTHER PUBLICATIONS

Tokarev, et al., (2009) "Stimuli-responsive hydrogel thin films", Soft Matter, vol. 5(3), (pp. 511-524).
Written Opinion of the International Searching Authority dated Aug. 5, 2014 for international application PCT/US2014/023352, filed on Mar. 11, 2014, and published as WO 2014/164731 on Oct. 9, 2014 (Applicant—University of Utah Research Foundation // Inventor—Tathireddy, et al.) (8 pages).
International Search Report mailed by the International Searching Authority dated Aug. 5, 2014 for international application PCT/US2014/023352, filed on Mar. 11, 2014, and published as WO 2014/164731 dated Oct. 9, 2014 (Applicant—University of Utah Research Foundation // Inventor—Tathireddy, et al.) (2 pages).
International Preliminary Report on Patentability mailed by the International Searching Authority dated Sep. 15, 2015 for international application PCT/US2014/023352, filed on Mar. 11, 2014, and published as WO 2014/164731 on Oct. 9, 2014 (Applicant—University of Utah Research Foundation // Inventor—Tathireddy, et al.) (9 pages).
U.S. Appl. No. 61/851,603, filed Mar. 11, 2013, Tathireddy (U. of Utah Res. Found.)
U.S. Appl. No. 61/927,683, filed Jan. 15, 2014, Tathireddy (U. of Utah Res. Found.)

\* cited by examiner

SENSOR SYSTEMS

CROSS REFERENCE TO RELATED APPLICATIONS

This application is a National Phase Under 35 U.S.C. § 371 of PCT/US2014/023352 filed in the Patent Cooperation Treaty U.S. Receiving Office on Mar. 11, 2014, which claims priority to U.S. Provisional Patent Applications No. 61/851,603 filed Mar. 11, 2013, and No. 61/927,683 filed Jan. 15, 2014, each of which is incorporated herein by reference in its entirety.

BACKGROUND

The present invention relates to sensor systems for detecting analytes and applications for such sensor systems.

There is a continuing need for improved sensor systems for medical and industrial purposes.

SUMMARY

In one embodiment, the invention provides a sensor sheath for a catheter. The sensor sheath includes a substrate having at least one sensor associated therewith; and an electronics unit in communication with the at least one sensor, wherein the substrate is configured to attach to a catheter.

In another embodiment the invention provides a sensor system. The sensor system includes a substrate having a least one hydrogel sensor associated therewith; a magnetometer adjacent the at least one hydrogel sensor; and a plurality of magnetic particles associated with the at least one hydrogel sensor.

Other aspects of the invention will become apparent by consideration of the detailed description and accompanying drawings.

DETAILED DESCRIPTION

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways.

In various embodiments, the present invention includes sensor systems for various applications including medical and industrial uses. In some embodiments, the sensor system includes at least one hydrogel sensor, and in particular embodiments the at least one hydrogel sensor is a smart hydrogel sensor, as discussed further below. In certain embodiments the sensor system is associated with a substrate, where the substrate may be part of a specialized sensor system such as a sheath for attaching to a catheter or a probe for use in a bioreactor.

Hydrogel Sensors

Figure 1:
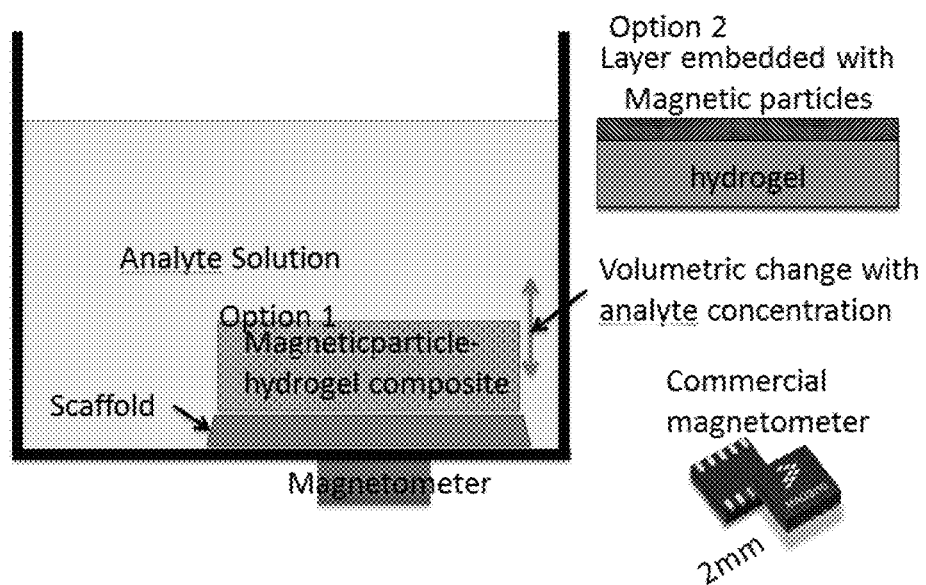
FIG. 1 shows an overview of a magnetic particle-hydrogel sensor system.
Figure 2:
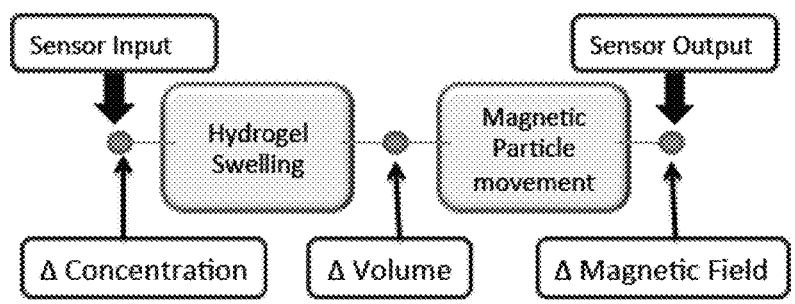
FIG. 2 shows a diagram of steps leading from a change in concentration of an analyte to a change in magnetic field in a magnetic particle-hydrogel sensor system.

Hydrogel sensors take advantage of a change in measurable properties of hydrogels upon interaction with a particular analyte (FIGS. 1-2). Generally, the analyte may interact with a hydrogel itself or a binding moiety within the hydrogel to provoke a change in a measurable property of the hydrogel, and information regarding the analyte may be extracted by measuring the change in the measurable property. Accordingly, the hydrogel-based sensor systems may include suitable mechanisms to detect the change in the measurable property.

Suitable hydrogels for use with this invention include any hydrogel that responds to the presence of an analyte with some change in at least one property of the hydrogel. In certain embodiments, the hydrogel may respond to the presence of an analyte with a change in physical properties, electrical properties, optical properties, mechanical properties, chemical properties or a combination thereof. In certain embodiments, the hydrogel may respond to the presence of an analyte with a change in size/volume, density, porosity, index of refraction, elasticity, viscosity, modulus or a combination thereof. In certain embodiments, the hydrogel may respond to the presence of an analyte by swelling or shrinking relative to its initial volume.

In certain embodiments, the hydrogel may respond to the presence of an analyte by swelling to occupy at least about 1.001 times its initial volume, at least about 1.01, at least about 1.1, at least about 1.2, at least about 1.3, at least about 1.4, at least about 1.5, at least about 1.6, at least about 1.7, at least about 1.8, at least about 1.9, at least about 2.0, at least about 2.5, at least about 3.0, at least about 3.5, at least about 4.0, at least about 4.5, at least about 5.0, at least about 6.0, at least about 7.0, at least about 8.0, at least about 9.0, at least about 10.0, at least about 11.0, at least about 12.0, at least about 13.0, at least about 14.0, at least about 15.0, at least about 20.0, or at least about 25.0 times its initial volume. In certain embodiments, the hydrogel may response to the presence of an analyte by swelling to occupy at most about 100 times its initial volume, at most about 90, at most about 80, at most about 75, at most about 70, at most about 65, at most about 60, at most about 55, at most about 50.0, at most about 45.0, at most about 40.0, at most about 35.0, at most about 30.0, at most about 29.0, at most about 28.0, at most about 27.0, at most about 26.0, at most about 25.0, at most about 24.0, at most about 23.0, at most about 22.0, at most about 21.0, at most about 20.0, at most about 19.0, at most about 18.0, at most about 17.0, at most about 16.0, at most about 15.0, at most about 14.0, at most about 13.0, at most about 12.0, at most about 11.0, at most about 10.0, at most about 9.0, at most about 8.0, at most about 7.0, at most about 6.0, or at most about 5.0 times it initial volume. This includes embodiments where the hydrogel responds to the presence of an analyte by swelling to occupy volumes ranging from about 1.001 to about 100 times its initial volume, including, but not limited to, volumes ranging from about 1.01 to about 50 times its initial volume, or volumes ranging from about 1.1 to about 25.0 times its initial volume.

In certain embodiments, the hydrogel may comprise a smart hydrogel. As used herein, the term "smart" refers to a hydrogel's ability to selectively bind one or more particular analyte species at the selective exclusion of one or more other species.

In certain embodiments, the hydrogel may comprise a material selected from the group consisting of synthetic materials, biological materials, biohybrid materials, and combinations thereof. In certain embodiments, the hydrogel may comprise a material selected from the group consisting of poly(acrylic acid) and derivatives thereof, poly(2-glucosyloxyethyl methacrylate) (poly(GEMA)) and derivatives thereof, poly(hydroxyethyl methacrylate) (PHEMA) and derivatives thereof, poly(ethylene glycol) (PEG) and derivatives thereof, poly(vinyl alcohol) (PVA) and derivatives thereof, polyacrylamide (PAAm) and derivatives thereof, poly(methacrylic) acid and derivatives thereof, poly(diethylaminoethyl methacrylate) and derivatives thereof, poly(dimethylaminoethyl methacrylate) and derivatives thereof, poly(N-isopropylacrylamide) (PNIPAAm) and derivatives thereof, Polyelectrolyte multilayers (PEM), Poly(2-oxazoline)s and derivatives thereof, and combinations thereof. In certain embodiments, the hydrogel may comprise a material selected from the group consisting of proteins, polysaccharides, DNA, and combinations thereof. In certain embodiments, the hydrogel may comprise a material selected from the group consisting of collagen, hyaluronic acid (HA), fibrin, alginate, agarose, chitosan, and combinations thereof.

In certain embodiments, the hydrogel may comprise one or more specific binding sites. The specific binding sites may be responsible for imparting the "smart" nature of a hydrogel. In certain embodiments, the specific binding site may comprise reversible or non-reversible binding sites.

Examples of suitable hydrogels for use with this invention include, but are not limited to, those disclosed in U.S. Pat. Nos. 5,415,864, 5,447,727, 6,268,161, 6,333,109, 6,475,750, 6,514,689, 6,753,191, 6,835,553, 6,848,384, 7,150,975, 7,179,487, 7,556,934, 7,625,951, 7,988,685, 8,221,773, 8,283,384, and 8,324,184, and U.S. Patent Application Pub. Nos. 2005/0169882, 2006/0239986, 2008/0206894, 2008/0044472, 2008/0275171, 2008/0311670, 2009/0170209, 2009/0215923, 2010/0285094, 2011/0044932, 2011/0280914, 2012/0170050, 2012/0029430, 2012/0234465, 2013/0129797, 2013/0143821, and 2013/0172985, and 2013/0267455, each of which is incorporated herein by reference in its entirety.

Catheter Sensors

In some embodiments the sensor system includes one or more sensors coupled to a substrate that is associated with a catheter (FIGS. 3-6). In one such embodiment, the hydrogels may be situated on a substrate that is part of a sheath which is associated with an outer surface of the catheter.

As discussed above, the hydrogels may be "smart" hydrogels which are chemically designed to reversibly and selectively bind to analytes dissolved in blood serum, such as fibrinogen and various clotting factors including, but not limited to, thrombin. Binding of an analyte to the appropriate hydrogel may be detected in a number of ways, generally involving detection of a change in size or pressure resulting from the binding of the analyte to the hydrogel, including piezoresistive pressure transducers, magnetometers (discussed below), or other means of converting the hydrogel size or shape change into an electrical signal. Other hydrogel changes that may occur include changes in impedance or fluorescence. By continuously monitoring these electrical signals, the serum concentration of analytes such as fibrinogen or various clotting factors such as thrombin may be accurately and rapidly determined as a function of time.

One particular use of a sensor system associated with a catheter relates to tests of blood coagulation that are used to monitor the anticoagulant effect of heparin or other anticoagulants infused into patients during heart surgery or during stays in critical care facilities. After a cardiovascular event such as a myocardial infarction or during heart surgery, it is common practice to infuse into a patient an anticoagulant such a heparin in order to reduce the risk of blood clots. For a given patient, the anticoagulant infusion rate must be continuously adjusted using the results of coagulation tests performed on the blood such as the Activated Clotting Time (ACT). In the ACT test, whole blood is intermittently removed from the patient, placed in a tube outside the body, and the time to clot is measured after addition to the blood of a clotting activator such as diatomaceous earth. The current technology for the ACT test suffers from limitations such as slow response time, intermittent measurements, and the necessity of removing the blood sample for analysis outside of the patient's body.

Another blood coagulation test that is more diagnostic than the ACT test is the endogenous thrombin generation test. Thrombin is the primary enzyme found in blood coagulation, and the endogenous thrombin generation test measures the conversion kinetics of a synthetic thrombin substrate. The current technology for the endogenous thrombin generation test also suffers from limitations such as slow response time, intermittent measurements, and the necessity of removing a blood sample from the patient's body. Methods have been proposed for the continuous measurement of the thrombin concentration in blood, using thrombin recognition elements such fibrinogen, aptamers for thrombin, and molecularly-imprinted aptamers for thrombin. However, the prior art does not teach a method for simultaneous and continuous measurement in vivo of the concentration of multiple clotting factors. Methods have also been proposed for the measurement of the soluble fibrinogen concentration in aqueous solutions. However, prior art does not teach a method for continuous real-time measurement in vivo of the fibrinogen concentration using stimuli-responsive hydrogels as a replacement for the ACT test.

The present embodiment of a sensor system provides a sensor array associated with an indwelling catheter for continuously measuring the concentration of fibrinogen, thrombin, and/or other various clotting factors within blood. The sensor array may contain several different types of stimuli-responsive (i.e. "smart") hydrogels for selective and reversible binding of the analytes of interest. In various embodiments, a stimuli-responsive smart hydrogel is a cross-linked polymer network that reversibly changes its properties in response to the change in a given environmental signal, including a change in the concentration of an analyte such as thrombin.

One way that a stimuli-responsive hydrogel can be fabricated to be responsive to a given analyte is using the process of molecular imprinting. In molecular imprinting, polymerization of a "functional" monomer is carried out in the presence of a porogenic solvent and the target analyte, the latter which is called the 'template'. After crosslinking/polymerization, the template is extracted, leaving behind cavities that contain a stereochemical arrangement of functional groups corresponding to the structure of the template. Hence the cavities will re-bind the analyte with high selectivity and sensitivity. For best results, a functional monomer needs be chosen that forms strong yet reversible physical bonds with the template molecule. Reversibility of analyte binding can be obtained by varying the identity and mole ratio of the functional monomers used to synthesize the imprinted hydrogel. For example, imprinted hydrogels can be obtained which reversibly bind proteins such as lysozyme, fibrinogen, and tumor-specific glycoproteins. For reversible binding of thrombin, suitable functional monomers can include methacrylic acid and 3-acryliamido phenyl boronic acid. The latter contains the boronic acid moiety which can reversibly bind to the glycosylated regions of thrombin.

Binding of the correct analyte(s) to the appropriate hydrogel will induce a change in a property of the hydrogel such as swelling degree, impedance, fluorescence, and/or magnetic field, each of which may be transduced into an electrical signal. These electrical signals can then be used to rapidly and continuously monitor the blood concentration of the analytes of interest. In some embodiments, in order to determine the ACT time blood will flow in or adjacent the catheter past a fibrinogen-responsive hydrogel after flowing through a porous bed of clotting activator such as diatomaceous earth. The clotting activator will initiate clotting and the subsequent incorporation of soluble fibrinogen into fibrin-based blood clots. Hence time-dependent clot formation and the ACT can be determined from the measured decrease in fibrinogen concentration. Alternatively, the increase in thrombin concentration can be measured from the signal obtained from the thrombin-responsive hydrogel and correlated to the endogenous thrombin potential. Because binding of the analytes to the hydrogels will be rapid and reversible, it will be possible to measure the value of the ACT and the endogenous thrombin potential continuously in vivo, which are distinct advantages relative to known systems.

Catheter Sheath

In one embodiment, a catheter-associated sensor system may include a sheath with one or more sensors attached thereto where the sheath can be attached to a catheter, for example by attaching to a side of, or wrapping around, the catheter (FIGS. 3-6). In certain embodiments, the sheath is fabricated using flex circuits (e.g. made of materials such as Parylene, Silicones, Polyurethanes, or Polyimides) so that the sheath can be wrapped around another structure such as a catheter. A sheath designed for catheter mounting may be elongated so that it can be wrapped around the shaft of the catheter.

Figure 3:
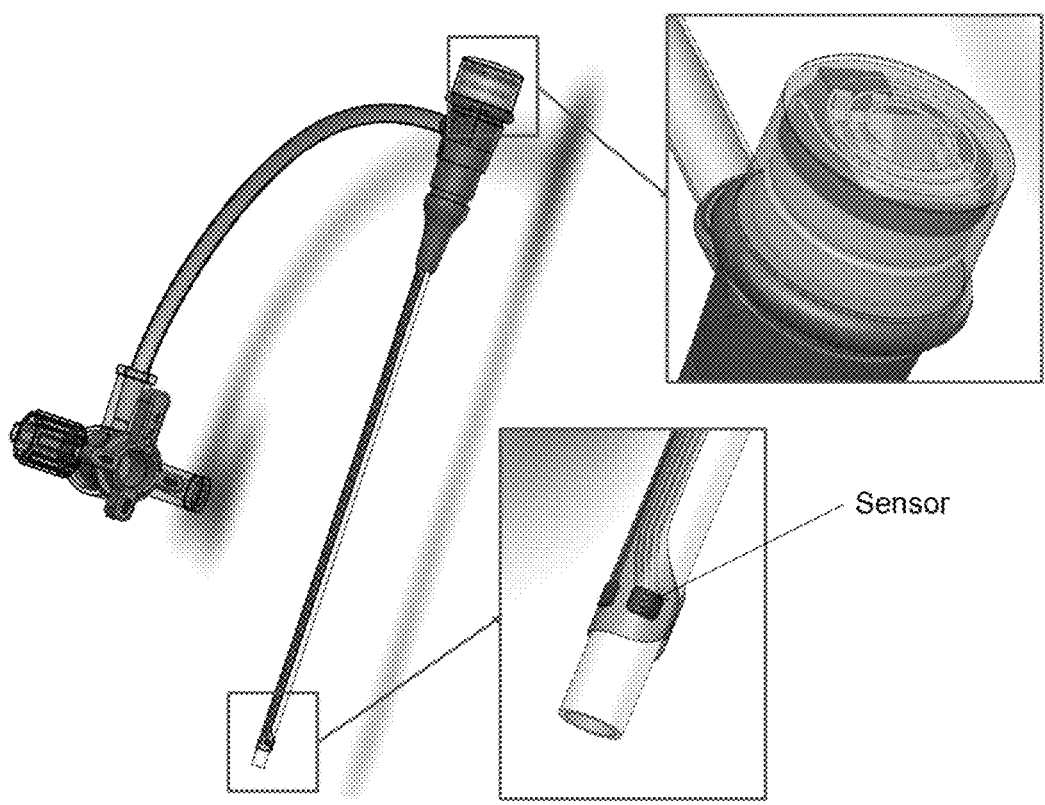
FIG. 3 shows a sensor system associated with a catheter using a sheath which wraps around the catheter.
Figure 5:
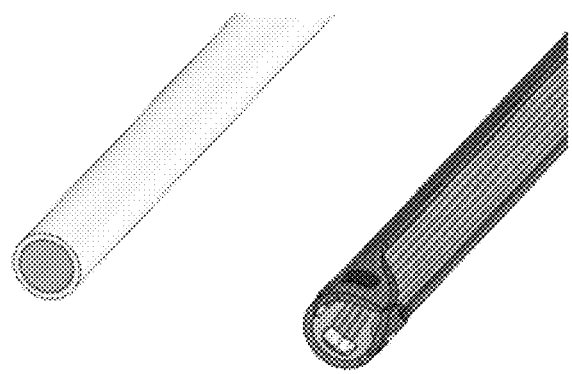
FIG. 5 shows a distal end of a catheter (left) and a distal end of a sheath (right) to which one or more sensors may be attached and configured to wrap around a catheter.

The sheath may wrap around the entire length of the catheter or just at the distal end (FIGS. 3, 5). To facilitate wrapping around the catheter, the sheath may be formed into a curled shape (for example during a curing process, e.g. using heat; see FIGS. 3, 5) or the sheath may be rolled and joined along the edge to retain the rolled shape, and/or the sheath may be attached to the catheter, e.g. using adhesive, to help maintain the curled shape.

Figure 6:
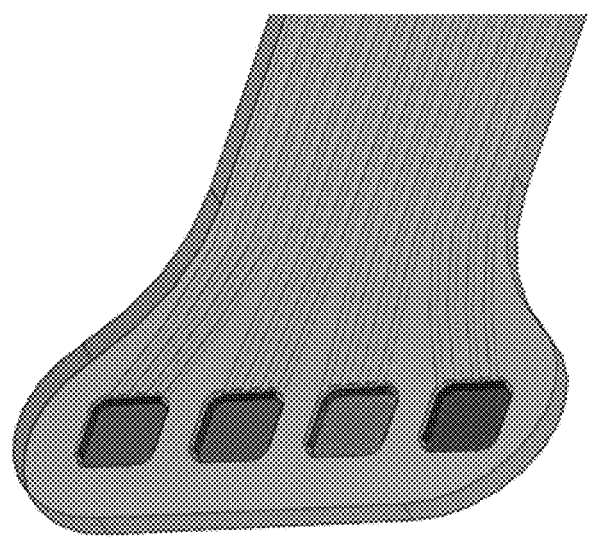
FIG. 6 shows a distal end of a catheter sheath, in a flattened configuration, showing several sensors along with electrical traces.

The sheath may have one or more sensors associated therewith, for example located at the distal end or disposed along its length (FIGS. 3, 5, 6). In some embodiments the sensors may include hydrogel sensors, and in one particular embodiment the sensors may be magnetic hydrogel sensors.

In the embodiment shown in FIGS. 3-6, the sheath includes a narrow body with a wide portion at a distal end. One or more sensors are attached to the sheath at the wide portion, which wraps around a distal end of the catheter (FIGS. 3, 5, 6). A plurality of electrical connections run from each sensor along the narrow body of the sheath to the proximal end, where the electrical connections connect with an electronics unit, which collects data from the sensors.

Figure 4:
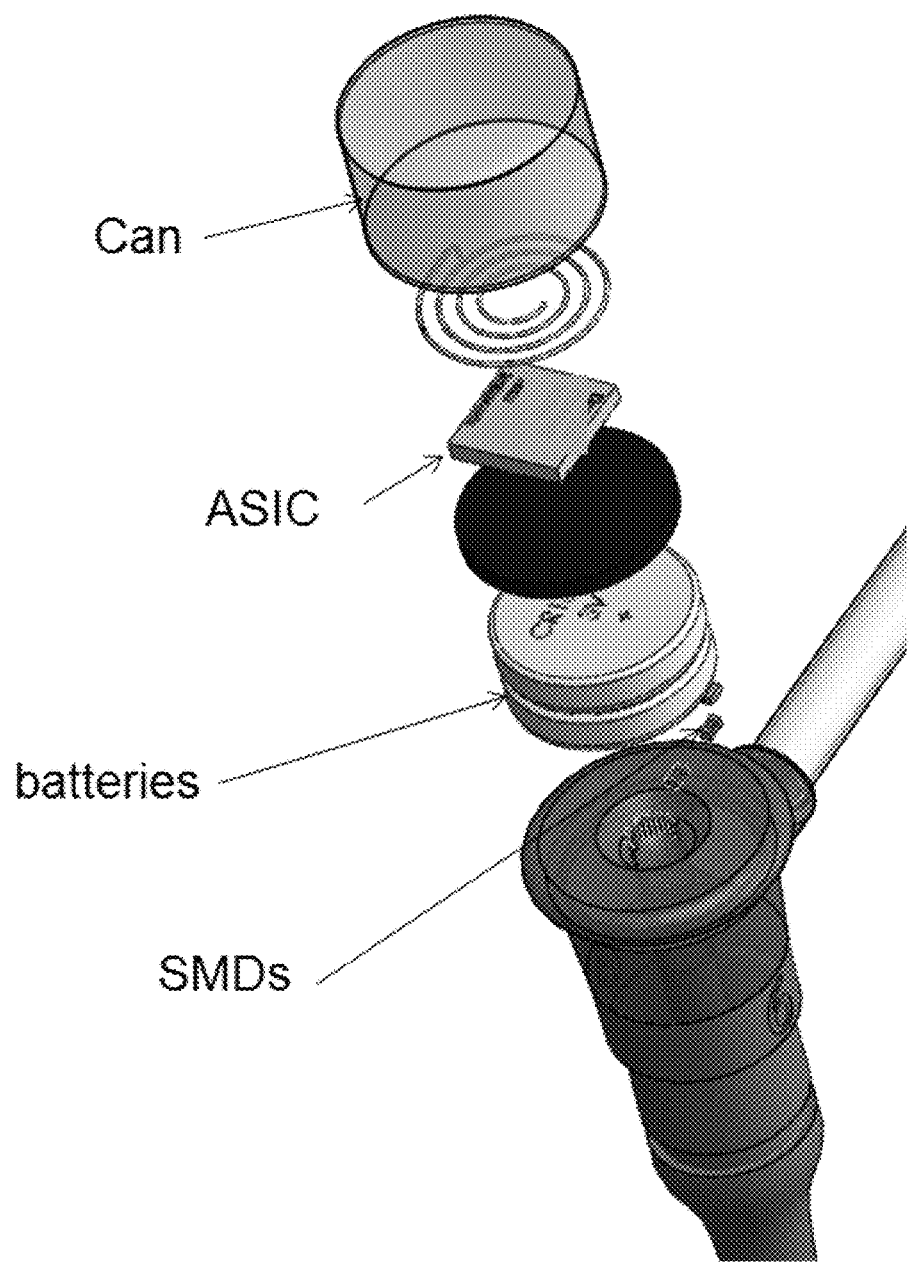
FIG. 4 shows an exploded view of an electronics system for use with a catheter-associated sensor system as shown in FIG. 3.

The electronics unit may also include a power supply (e.g. one or more batteries) and a telemetry system including an antenna for wireless communications (e.g. for receiving commands and transmitting data) (FIG. 4). Wireless communications may be conducted using any number of suitable protocols such as Bluetooth or ZigBee. The electronics unit may communicate with other computers or smartphones that are local or remote from the sheath using wireless communications or in a wired configuration. Data transfer may be initiated in several ways, including by activation of a touch-sensitive switch on the electronics unit. The electronics unit may be housed in a small package that can be mounted at an end of the catheter, for example distal from the location of the sensors. In some embodiments the narrow body of the sheath may extend through a coupling of the catheter and connect to the electronics unit inside the coupling (FIG. 4).

In particular embodiments, the sheath may be made of one or more flexible and/or biocompatible materials (e.g. Parylene, Silicones, PU, PI) and has embedded therein electrical traces and interconnects from the sensor array to a circular processor unit. The processor unit may be dimensioned such as to fit exactly on the top part of the catheter structure, extending the length by less than 5 mm.

Various types of sensors can be used with the sheath, although in one particular embodiment the sensors include smart hydrogels with magnetic particles associated therewith in which a magnetometer is used to detect changes in the hydrogel due to interaction with the analyte (see below). In various embodiments the sensors that may be used with the sheath include amperometric (current), potentiometric (voltage), optical (e.g. fluorescence), mechanical (e.g. pressure, volume), magnetic, and inductive (RF frequency shift) sensors. In addition to hydrogels, sensing mechanisms may include various enzymatic and non-enzymatic mechanisms including those employing antibodies and other protein-based sensors.

The disclosed catheter sheath sensor system allows intraprocedural, real-time monitoring of changes in electrolytes, blood coagulation status, and injury markers (enzyme etc.) and will save a significant amount of blood draws, additional testing and ensure a higher level of safety by detecting changes in critical blood values as they happen in real-time.

Bioreactor

Figure 7:
FIG. 7 shows an embodiment of a sensor system which is mounted at the end of a probe, for example for use in a bioreactor.

When used as part of a bioreactor, an array having one or more sensors is located at the end of a probe to be inserted into the bioreactor (FIG. 7). In some embodiments the probe may have two or more separate portions including a disposable sleeve containing one or more sensors (e.g. hydrogel sensors) and a magnetic detector insert which is inserted into the sleeve. In this configuration, the sleeve interacts with the contents of the bioreactor while the magnetic detector insert is shielded from the contents and therefore can be reused. In this configuration it is particularly advantageous to use magnetic hydrogel sensors such as those disclosed herein, because the magnetic detectors can monitor changes in the magnetic particles associated with the hydrogel sensors without making direct contact. When the magnetic detector insert is inserted into the sleeve, the sensors on the sleeve align with the array of magnetic detectors on the insert, permitting the magnetic sensors to 'interrogate' the magnetic hydrogels. The sleeve in various embodiments may include a porous end portion (e.g. a hemispherical mesh cover as shown) which permits passage of analytes so that the analytes can interact with the sensors while protecting the sensors. The electronics for controlling the sensors may be included in the insert portion of the probe adjacent to the magnetic detectors or may be at a remote location.

Magnetic Particle-Based Hydrogel Sensors

In certain embodiments, the sensor system includes magnetic hydrogel sensors. Magnetic hydrogel sensors use hydrogels, including smart hydrogels, as described above, in which the hydrogel changes shape due to its interaction with an analyte, and detection of the change in the measurable property is detected using magnetic particles, including nanoparticles, associated with the hydrogel.

Thus, the volumetric response of stimuli-responsive hydrogels can be monitored by measuring the change in magnetic field intensity (MFI) by the embedded magnetic nanoparticles. Results indicate that it is possible to construct a hydrogel-magnetic particle composite and measure the changes in MFI with the changes in density of magnetic particles and distance from the magnetometer.

The disclosed techniques provides a unique combination of magnetic sensors with analyte-responsive hydrogels. Nanoparticles have previously been embedded in hydrogels as part of controlled drug-delivery applications, although the techniques disclosed herein are versatile and can be used in a wide range of applications. As noted above, the specific chemistry of the synthesized hydrogels causes them to respond to a unique stimulus (e.g. interaction with an analyte) by swelling or deswelling up to 300% their original volume in proportion to the concentration or intensity of the stimulus.

In some embodiments, the magnetic particles or nanoparticles may be arranged in a particular alignment in or adjacent to the hydrogel. For example, in one embodiment the sensor system includes a smart hydrogel having magnetic nanoparticles embedded therein, where the magnetic fields of the nanoparticles are vertically aligned. The vertically aligned magnetic nanoparticles embedded in the smart hydrogels will transduce the hydrogel actuation as a change in magnetic field intensity in and around the hydrogel, which is detected by a magnetometer adjacent to the hydrogel (FIGS. 1, 2). This approach provides several advantages relative to other techniques for monitoring hydrogels such as monitoring pressure changes caused by swelling of the hydrogel, chemical sensing techniques (e.g. electrochemical methods), and optical sensing techniques. The hydrogels can be adapted in a number of ways to respond to concentrations of almost any analyte, expanding the potential impact of the proposed technique enormously.

Figure 8:
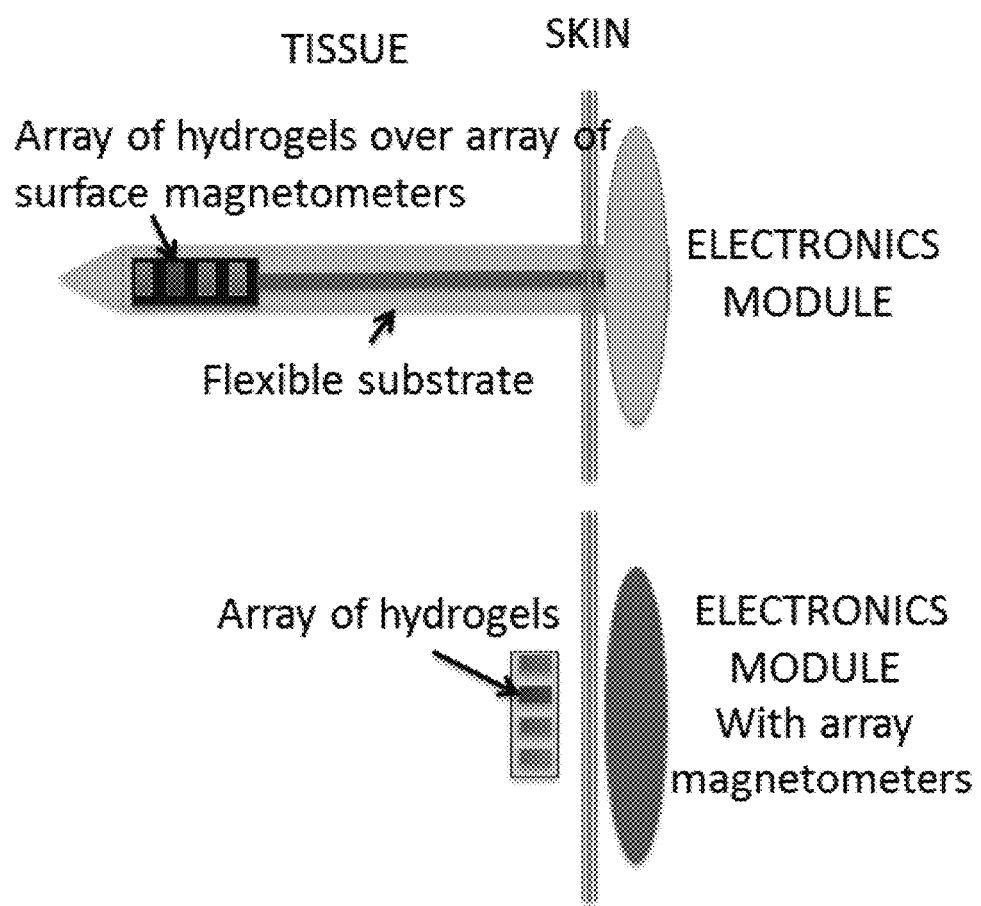
FIG. 8 shows an embodiment of a sensor system which can be mounted under a subject's skin, with a magnetometer for measurement being located either under (top) or over (bottom) the subject's skin.
Figure 9:
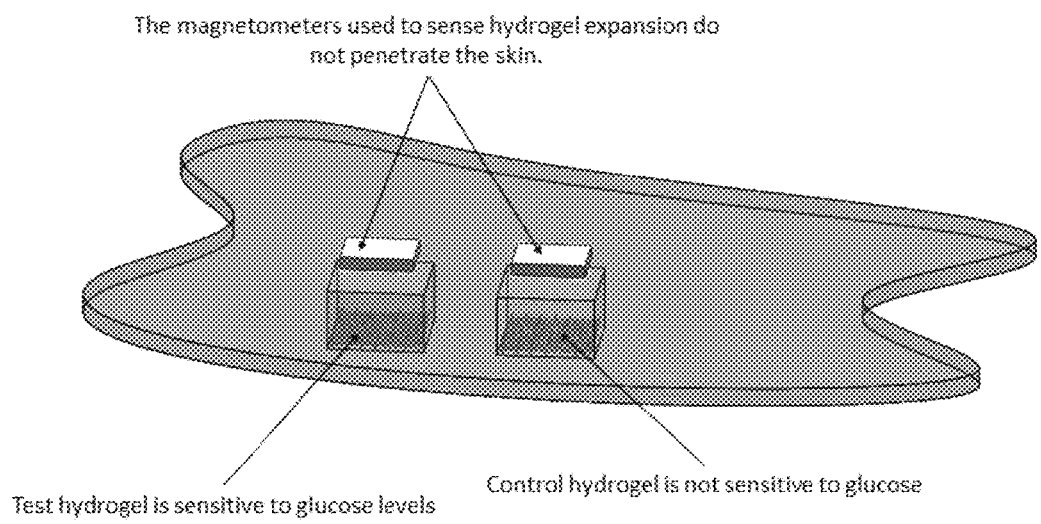
FIG. 9 shows another embodiment of a sensor system for use adjacent a subject's skin.

One advantage of the disclosed magnetic nanoparticle hydrogel sensor system is its ability to respond to multiple analytes using different hydrogels within the same sensor platform and its adaptability to a wide variety of sensing applications such as in bioreactor composition sensing, point-of-care medical treatment, or as fully-implantable, chronic (continuous) sensors of physiological biomarkers to monitor diseases or treatment states. For example, passive 'magnetic-hydrogel' composites may be implanted in a subject's subcutaneous region and active components may be placed on the skin surface for long-term continuous monitoring of biomarkers (FIG. 8). In one embodiment an array of sensors may be implanted under a subject's skin with a wired connection to an electronics unit outside the surface of the subject's skin (FIG. 8, top). In another embodiment, an array of magnetic particle-hydrogel sensors is implanted under the subject's skin and a magnetometer and electronics unit is placed over the hydrogel sensors to detect changes in the magnetic fields induced by analyte-dependent changes in the hydrogels (FIG. 8, bottom). In one particular embodiment a pair of magnetic particle-hydrogel sensors may be implanted near one another, with one being sensitive to an analyte (e.g. glucose) and the other being analyte-insensitive (FIG. 9). Magnetometer readings are then collected from both sensors and a differential signal is determined based on the pairs of readings, canceling out changes in signal due to factors other than changes in analyte level, such as the subject's hydration level and body temperature, among other factors. Sensors may be located in a subject's skin in one or more locations throughout the subject's body including in the arms, legs, torso, or head (including, for example, the earlobe).

Figure 10:
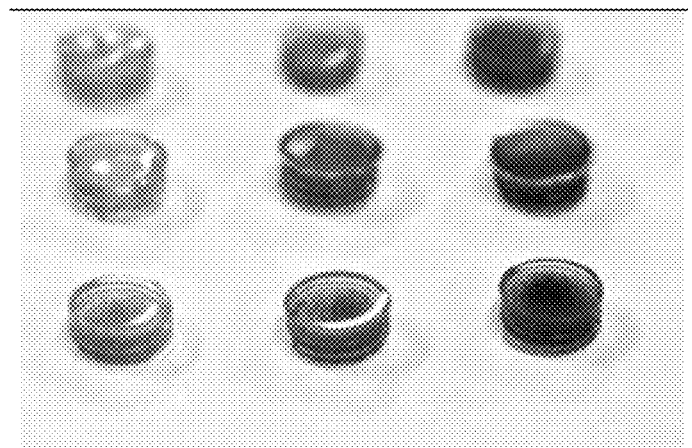
FIG. 10 shows a series of test samples of hydrogel having concentrations of 0.25% (left), 0.50% (center), or 1.0% (right) (w/w) of magnetic particles.
Figure 11:
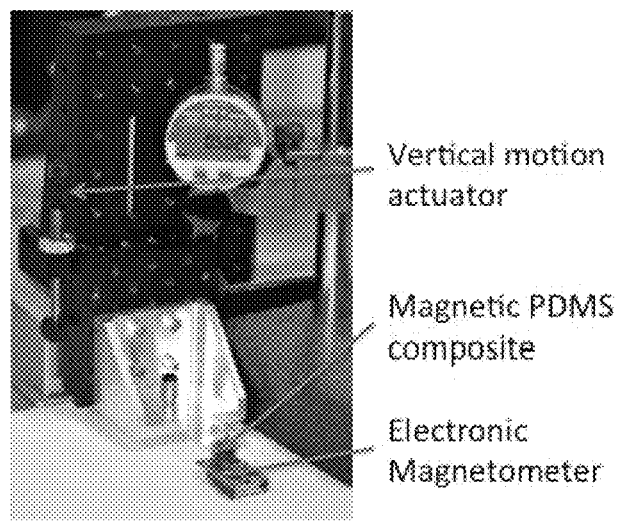
FIG. 11 shows an experimental setup for initial testing of magnetic field strength of samples such as those shown in FIG. 10.
Figure 12:
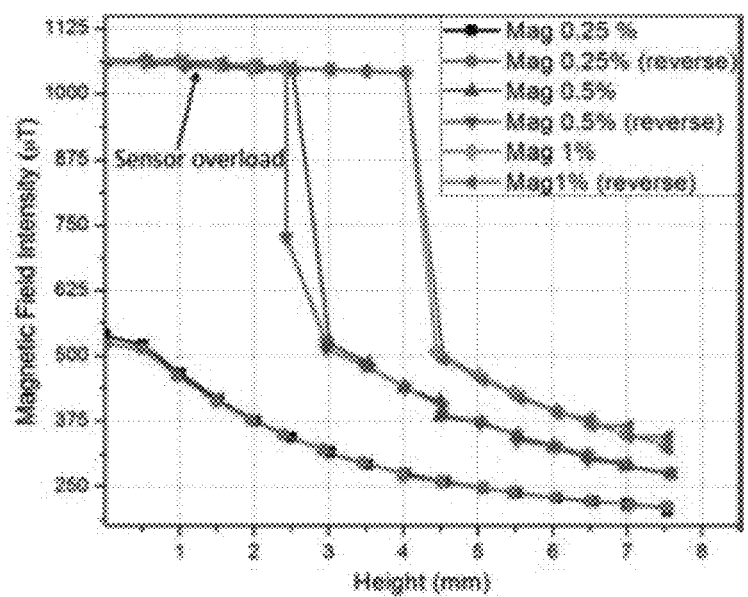
FIG. 12 is a graph of magnetic field strength vs. distance using the setup of FIG. 11 and the samples of FIG. 10.

Preliminary experiments support the many advantages of the disclosed technique. In these experiments processes have been developed to disposed magnetic nanoparticles within a 2 mm thick layer of polydimethylsiloxane (PDMS) and align the particles in strong external magnetic field before the PDMS is completely cured (generally using thermal techniques). Three PDMS composite samples were built for three different concentrations (0.25%, 0.5%, 1% w/w) of magnetic particles (N=3×3) and changes in magnetic-field intensity with distance were measured using a commercial magnetometer for all samples (FIGS. 10, 11). These initial experiments were conducted using a commercially-available coarse triple axis magnetometer (HMC5883L from Honeywell), although other types of magnetic sensing systems may be used. As seen from the results the sensor is overloaded or saturated in the presence of the 0.5% and 1% composites at closer distances (FIG. 12). However it should be noted that (1) there is no hysteresis (a major problem with current techniques) in the measurements, (2) there is a significant (easily resolvable) difference in the field intensity between all the concentrations tested at any particular distance. These initial results convincingly support the listed advantages.

Figure 13:
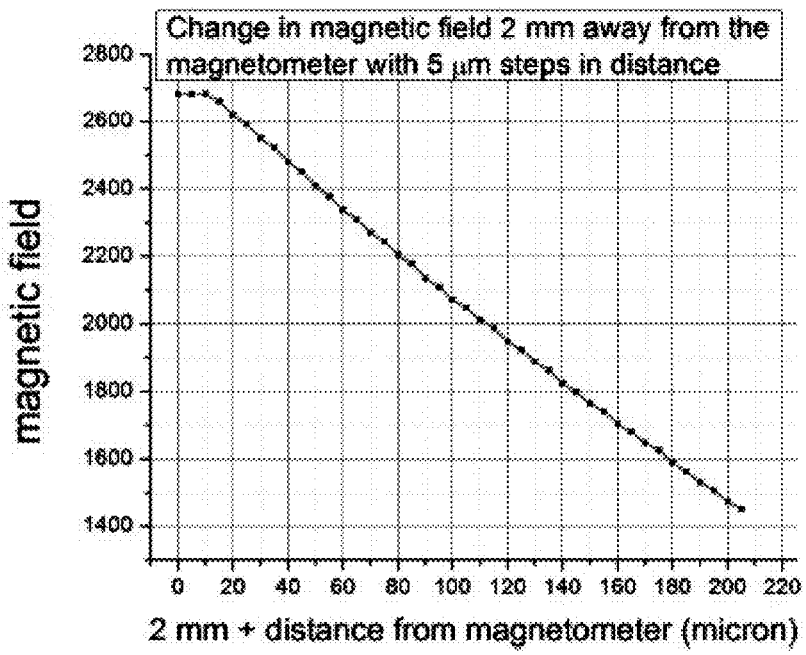
FIG. 13 shows changes in magnetic field strength as a function of distance
Figure 14:
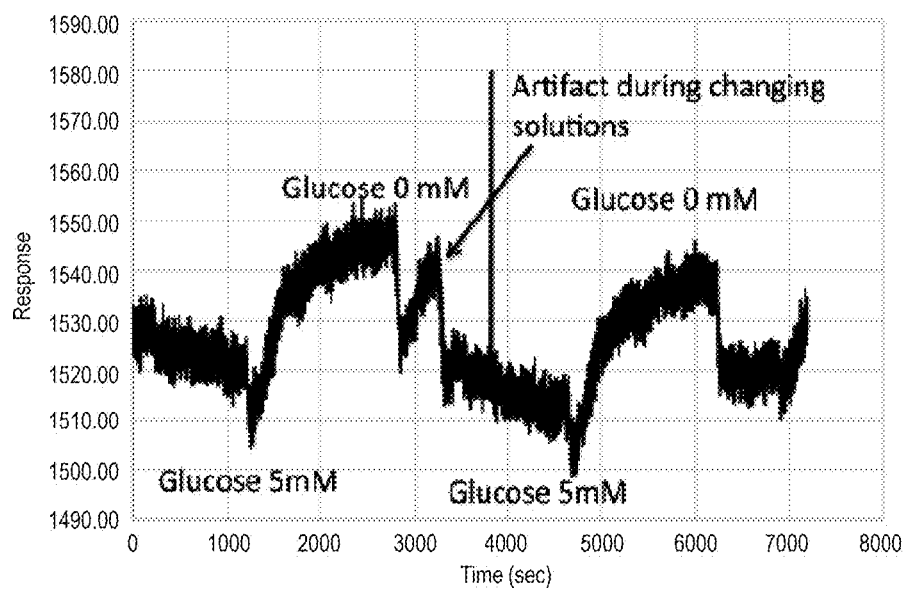
FIG. 14 shows changes in glucose concentration measured using a glucose-sensitive magnetic particle hydrogel.
Figure 15:
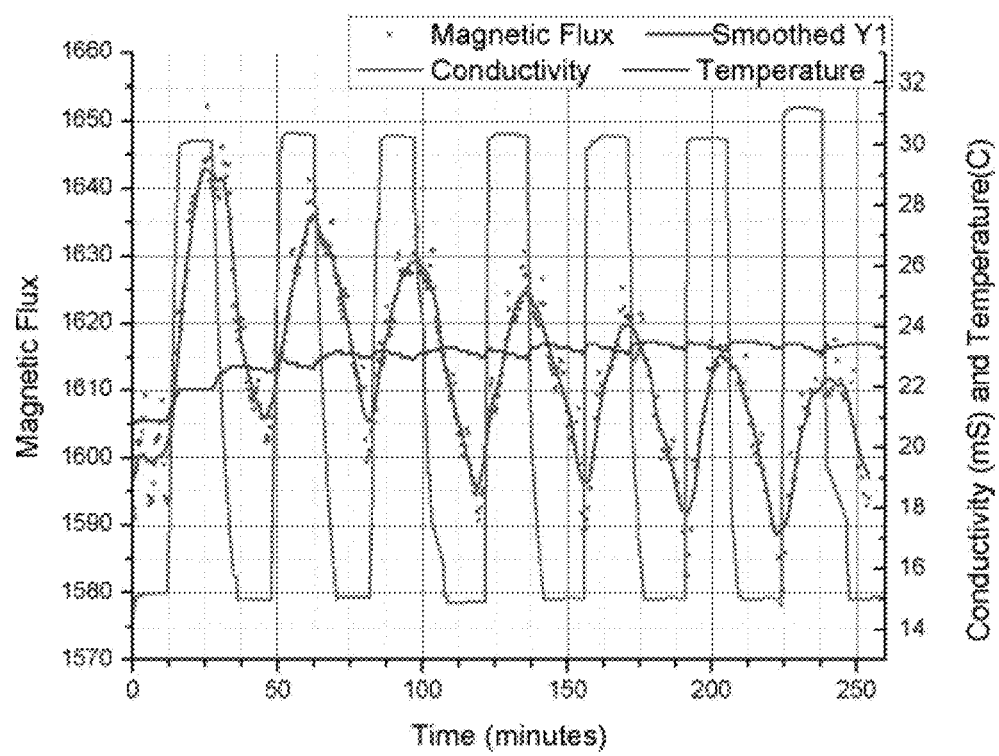
FIG. 15 shows changes in ionic strength measured using an ionic strength-sensitive magnetic particle hydrogel.

Other experiments show the high sensitivity of the magnetic field measurements as a function of distance from the magnetometer (FIG. 13) as well as the sensitivity of the system using a glucose-sensitive magnetic particle hydrogel (FIG. 14) or an osmotic strength-sensitive magnetic particle hydrogel (FIG. 15). FIG. 13 shows the sensitivity of an off-the-shelf magnetometer. Measured changes in the magnetic field are due the movement of a magnetic strip by 5 micrometer increments 2 mm above the magnetometer. The magnetic strip was moved using an automatic (computer controlled) linear actuator 20 times from 0-200 micrometers and the data shows excellent repeatability. This experiment was conducted to demonstrate the ability of magnetically measuring fine physical movements relatively far away (three orders of magnitude) from a low-cost magnetometer. FIG. 14 demonstrates the ability to measure the changes in glucose concentration using a magnetic-hydrogel. In this case the hydrogel is synthesized to be glucose responsive and a prefabricated magnetic film was placed over the hydrogel to form the magnetic hydrogel. The hydrogel was attached to the inside wall a glass-beaker while the magnetometer was aligned to the hydrogel on the outside of the beaker. At a constant pH of 7.3 and in a constant 1× phosphate buffered solution, glucose concentration was changed from 0 mM to 5 mM and the resulting change in the magnetic field was measured using the magnetometer. The solution in the beaker was mildly stirred throughout the experiment. The data artifact seen after the first cycle in FIG. 14 is caused during the act of changing solutions in the beaker. The setup used in experiment that resulted in FIG. 15 is similar to that described above for FIG. 14. Here the hydrogel used was one sensitive to ionic strength. Ionic strength was changed using an automatic flow control system from 1× to 2×PBS in the beaker and the change in magnetic field was measured using the magnetometer. The drift in the data is caused due to the conditioning of the hydrogel.

The number and variety of applications of the disclosed magnetic nanoparticle-hydrogel sensor system is enhanced by the ongoing research and development of hydrogel properties and specificities, which will help in the application of this invention in medical device/diagnostic field, among others.

In various embodiments, the disclosed sensors may be adapted for use in a variety of fields. In the neurology and psychiatry fields, sensors may be adapted for diagnosing and monitoring symptoms related to addiction, depression, Parkinson's disease, stroke, and blood pressure. In the oral/gastrointestinal field, sensors may be adapted for detection of smoking, monitoring intake of various medications and other drugs, and monitoring changes in acid levels in the esophagus and stomach. In the pulmonology field, sensors may be adapted for monitoring of inhalers as well as diagnosis, monitoring, and management of symptoms related to conditions of the lungs such as asthma and chronic obstructive pulmonary disease (COPD).

In the cardiac field, sensors may be adapted for use related to interventional procedures such as monitoring of pH, electrolytes, glucose, troponin, C-reactive protein, troponin, cholesterol components, and guidance and monitoring use of anticoagulants such as monitoring of factors Xa and thrombin. Also in the cardiac field, sensors may be adapted for use with devices such as ICD leads (e.g. for sensing of heart failure and heart attacks), PM leads (e.g. for monitoring of heart failure and heart attacks), and for monitoring clot formation including thrombin generation (thrombin-antithrombin [TAT] complex), endothelial dysfunction (asymmetric dimethylarginine [ADMA]), and platelet-derived inflammation (soluble CD40 ligand [sCD40L]).

In the hepatology field, sensors may be adapted for monitoring and/or diagnosing liver enzymes, hepatitis C, fat liver, and liver transplants; in addition, pancreatic activity can be evaluated through monitoring of blood glucose levels in order to assess an individual's or population's diabetes risk level. In the renal field, sensors may be adapted for measuring creatinine levels, monitoring kidney transplants, and monitoring the physiology of dialysis patients. In the hematology field, sensors may be adapted for monitoring iron and hemoglobin levels as well as diagnosing and monitoring treatment of blood cancers (e.g. detecting particular markers). In the urology field, sensors may be adapted for monitoring the prostate including PSA levels. Finally, sensors may be adapted for use before, during, and after surgery to monitor a subject's levels of pH, electrolytes, blood anticoagulation factors, hemoglobin, and lactate levels.

Among the advantages of the disclosed magnetic nanoparticle-hydrogel sensor system:

(1) No by-products: Unlike electrochemical sensing, the disclosed methods do not produce by-products from the sensing mechanism;

(2) Long lifetime: Unlike other common sensing techniques that consume raw materials during sensing, the disclosed hydrogel-based sensing technique does not depend on chemical reactions;

(3) Response to multiple analytes: A particular advantage of the proposed approach is its ability to respond to multiple analytes using different hydrogels within the same sensor platform and its adaptability to a wide variety of sensing applications such as in bioreactor composition sensing, point-of-care medical treatment, or as fully implantable, chronic sensors of physiological biomarkers to monitor diseases or treatment states; and (4) Minimum exposure to exogenous materials: In medical device applications, the disclosed sensors are expected to have fewer problems due to a subject's body reacting to foreign objects associated with the sensor because the implanted portion can be as little as the passive hydrogel portion, while the remaining detection components (e.g. the magnetometer and related electronics) can be placed on the surface of the subject's body/skin.

Among the many possible applications for the disclosed magnetic nanoparticle-hydrogel sensor system:

(1) Bioreactor composition sensing, especially for one-time use reactors;

(2) Point-of-care medical treatment;

(3) Fully implantable, chronic/continuous sensors of physiological biomarkers to monitor disease states or progress of treatments; and (4) Continuous metabolic sensing in animal research.

One possible limitation of the disclosed magnetic nanoparticle-hydrogel sensor system is possible interference when used in high magnetic-field environments, such as in or near MRI systems. The sensing MFI range of the proposed sensor in some embodiments may range from about 300 µT to about 4000 µT. While this range is much higher than the earth's magnetic field range (25-65 µT), it is lower than that seen in magnetic resonance imaging (MRI). Sensor readings may be influenced by strong external magnetic fields, although one way to overcome this limitation may be to have an auxiliary reference magnetometer at a distance from the sensor, for example in a hand-held monitoring device, so that differential magnetic readings can be taken.

Figure 16:
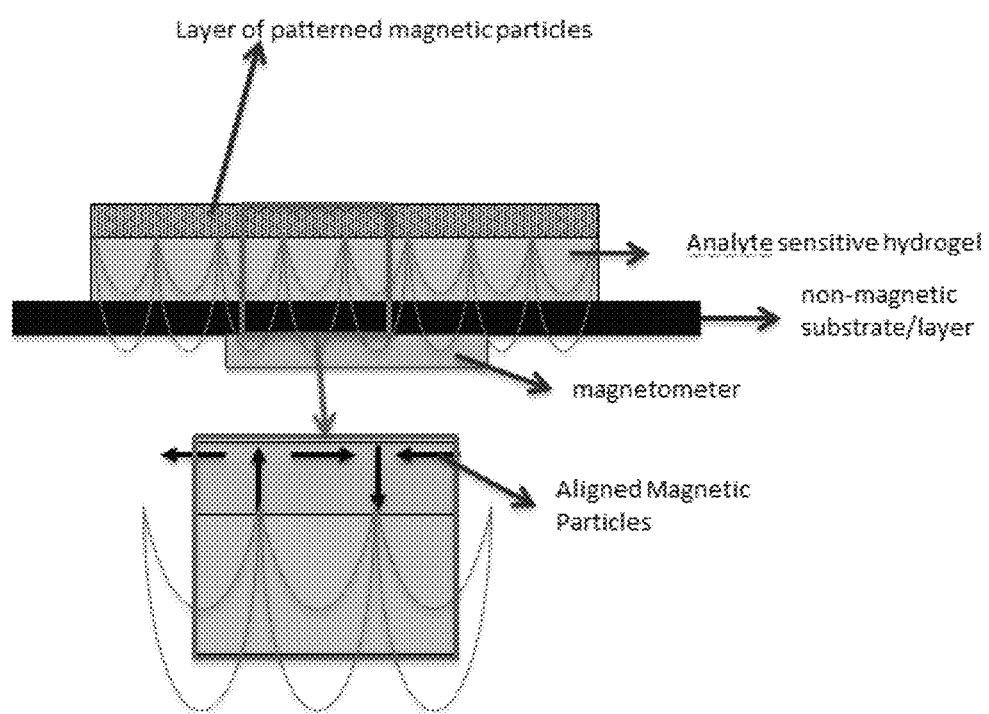
FIG. 16 shows alignment of magnetic particles in a hydrogel in a Halbach array.
Figure 17:
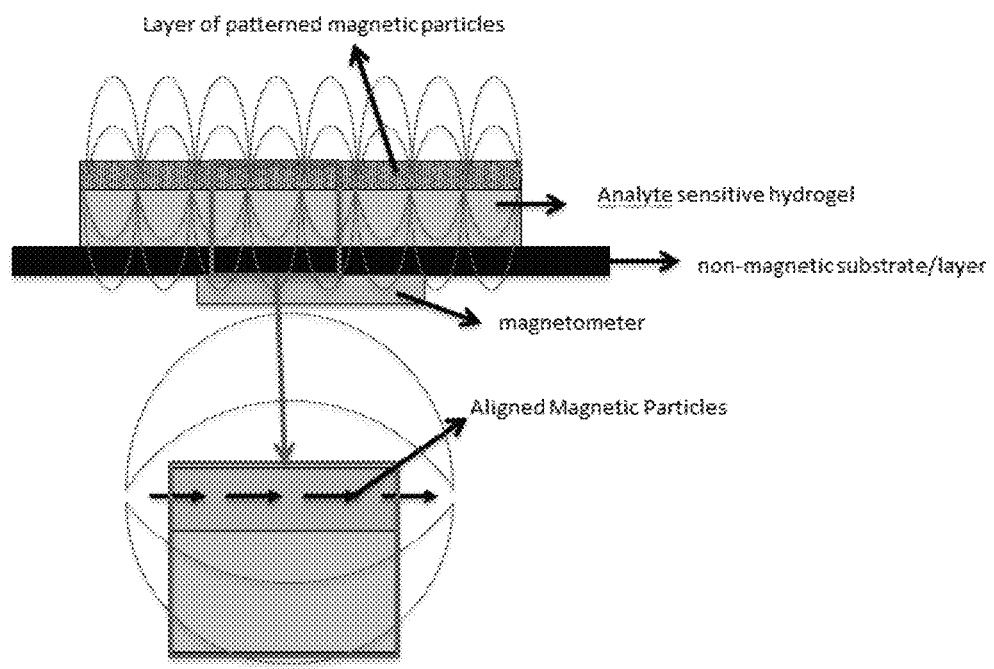
FIG. 17 shows alignment of magnetic particles in a hydrogel in a uniform array.

FIGS. 16 and 17 show alignment of magnetic particles in or adjacent to a hydrogel. FIGS. 16 and 17 each show a hydrogel mounted on a substrate with a layer containing magnetic particles on top of the hydrogel. The hydrogel may be continuously attached to the substrate during use, or the substrate may only be present during formation of the hydrogel and removed from the hydrogel prior to use. In some embodiments, a larger portion of the hydrogel (with or without a separate top layer) may be made and then divided into smaller sections for use. In use, a magnetometer is placed near the hydrogel, for example under the substrate, when present, or near the hydrogel, to detect magnetic fields from the particles associated with the hydrogel.

Figure 18:
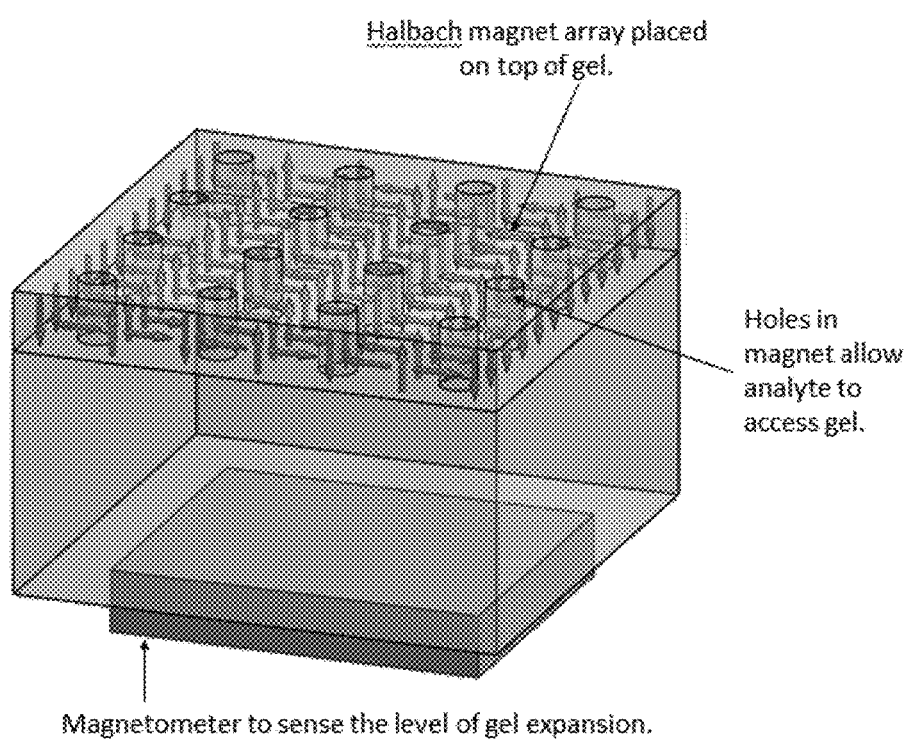
FIG. 18 shows a particle-containing layer on top of a hydrogel in which the particle-containing layer is perforated to permit the analyte to access the hydrogel.

Although the magnetic particles are contained in a layer on top of the hydrogel, in some embodiments the hydrogel itself (or a portion thereof) may contain the particles. The particle-containing layer, when present, may be solid or it may be porous or contain perforations to permit access by the analytes to the hydrogel (FIG. 18). The particle-containing layer may be made of a hydrogel (the same or different from the underlying hydrogel), another polymer, or silicone, among various possible materials.

In certain embodiments, a hydrogel and/or top layer may be formed according to the following procedures:

(1) Prepare the pre-gel (hydrogel, silicone, epoxy, etc.) and mix magnetic particles to form a homogenous solution;

(2) Form a thin layer of solution on a substrate and ensure that the magnetic particles are uniformly dispersed;

(3) Subject the film to an external magnetic field with desired field pattern during the polymerization process to ensure that particles in the polymerized layer are aligned;

(4) If formed as a separate layer, this layer may then be placed over an analyte-sensitive hydrogel.

The depth of the plane along which the particles are aligned may be altered by controlling the magnitude of the externally-applied magnetic fields during the curing process.

The magnetic particles in FIG. 16 are arranged in a Halbach array (FIG. 16, inset). The particular arrangement of particles (e.g. with adjacent vertically-aligned and horizontally-aligned particles having their magnetic fields in opposite directions) causes the magnetic field to extend primarily in one direction away from the plane of the hydrogel or particle layer. FIG. 17 shows another arrangement in which the particles are uniformly aligned, for example horizontally, as shown (FIG. 17, inset), or vertically. In the case of a uniform particle arrangement, the magnetic fields extend relatively equally in both directions away from the plane of the hydrogel or particle layer. In various embodiments, the operating distance at which the magnetic fields are detectable range from tens of micrometers to several millimeters from the particles.

The Halbach array or uniform magnetic field may be generated in the layer or hydrogel by subjecting the layer or hydrogel to a suitable magnetic field during curing. In particular, the Halbach array particle arrangement may be realized in one of several possible ways: (1) one way to generate this array is to dispense ferromagnetic particles in a polymer homogeneously and form a magnetic composite sheet, as discussed above, and then magnetize the sheet using a magnetizer with a pre-configured pattern. Polymers that can be used, for example but not limited to, are silicones, polyurethanes, polyethylenes, hydrogels, and other polymers; (2) another way is to select a prefabricated, commercially-available Halbach array sheet material and use it to 'mirror' its magnetic arrangement into the hydrogel. This may be accomplished by uniformly dispersing permanently magnetized particles on a selected Halbach array, making sure the particles form an array pattern on the sheet. Then the hydrogel pre-gel solution can be dispensed on the sheet containing arranged magnetic particles, followed by polymerization of the pre-gel solution to form a magnetic hydrogel composite. Magnetic particles may be surface modified to polymerize with the pre-gel solution and/or to promote biocompatibility.

In various other embodiments, other arrangements of magnetic particles which maximize the magnetic field gradient are also possible, including a setup having an internal and external (to hydrogel) arrangement of magnetic particles/source to (1) shield noise (2) improve the magnetic field gradient.

Possible magnetic nanoparticle materials include permanent magnetic particles such as ferro- or ferri-magnetic particles, rare-earth alloys (samarium-cobalt, neodymium-iron-boron), ceramic ferrites (barium or strontium ferrite), and other magnetic materials. The magnetic particle/nanoparticle sizes may range from 20 nm to tens of micrometers, with a typical size being about 1 micrometer. In various embodiments the magnetic particle/nanoparticle concentration range, in either the hydrogel and/or in a separate film layer, is up to 10% by weight. A non-limiting list of analytes that the hydrogel may interact with include glucose, fructose, ionic strength/osmolality, oxidative stress, hydration, pH, $CO_2$, $O_2$, lactate, thrombin and other proteins, and particular cell types. The hydrogel-based sensor systems disclosed herein may be used to determine the presence and levels of the various analytes.

Various features and advantages of the invention are set forth in the following claims.

What is claimed is:

1. A sensor system, comprising:
   a substrate having at least one hydrogel sensor associated therewith;
   a magnetometer adjacent the at least one hydrogel sensor; and
   a plurality of magnetic particles associated with the at least one hydrogel sensor,
   wherein the plurality of magnetic particles is arranged in a uniform alignment such that the magnetic fields of the plurality of magnetic particles are aligned in a same direction without applying an external magnetic field, and
   wherein an operating distance at which the magnetic fields are detectable by the magnetometer ranges from tens of micrometers to several millimeters from the plurality of magnetic particles.

2. The sensor system of claim 1, wherein the magnetic fields of the plurality of magnetic particles are aligned in a Halbach array.

3. The sensor system of claim 1, wherein the plurality of magnetic particles comprises magnetic nanoparticles.

4. The sensor system of claim 1, further comprising an electronics unit in communication with the at least one hydrogel sensor.

5. The sensor system of claim 1, wherein the magnetic particles are embedded within the at least one hydrogel sensor.

6. The sensor system of claim 1, wherein the magnetic particles are in a layer on top of the at least one hydrogel sensor.

7. The sensor system of claim 1, wherein the at least one hydrogel sensor is sensitive to an analyte.

8. The sensor system of claim 7, wherein the analyte is protein, glucose, fructose, ionic strength/osmolality, oxidative stress, hydration, pH, CO2, O2, lactate, thrombin, fibrinogen, factor Xa, clotting factor, blood anticoagulation factor, thrombin-antithrombin complex, asymmetric dimethylarginine, soluble CD40 ligand, tumor-specific glycoprotein, C-reactive protein, creatinine, iron, hemoglobin, prostate-specific antigen, electrolyte, cholesterol components, or physiological biomarker.

9. The sensor system of claim 1, wherein the substrate comprises multiple hydrogel sensors sensitive to multiple analytes.

10. The sensor system of claim 1, wherein the sensor system is adapted for use in bioreactor composition sensing, point-of-care medical treatment, or as fully implantable, chronic/continuous sensor of physiological biomarker to monitor disease state or progress of treatment.

11. A probe, comprising the sensor system of claim 1.

12. The probe of claim 11, further comprising a disposable sleeve, wherein the at least one hydrogel sensor is located on the disposable sleeve.

13. The probe of claim 11, wherein the magnetometer is adapted to insert into the disposable sleeve.

* * * * *